United States Patent [19]
Gladfelter et al.

[11] Patent Number: 5,191,099
[45] Date of Patent: Mar. 2, 1993

[54] CHEMICAL VAPOR DEPOSITION OF ALUMINUM FILMS USING DIMETHYLETHYLAMINE ALANE

[75] Inventors: Wayne L. Gladfelter, St. Paul; Everett C. Phillips, Minneapolis, both of Minn.

[73] Assignee: Regents of the University of Minnesota, Minneapolis, Minn.

[21] Appl. No.: 755,317

[22] Filed: Sep. 5, 1991

[51] Int. Cl.$^5$ ............................................. C07F 5/06
[52] U.S. Cl. ........................................ 556/27; 556/176
[58] Field of Search ................................ 556/27, 176

[56] References Cited

U.S. PATENT DOCUMENTS

| | | |
|---|---|---|
| 3,206,326 | 9/1965 | Whaley et al. . |
| 3,375,129 | 3/1966 | Carley et al. . |
| 3,462,288 | 8/1969 | Schmidt et al. . |
| 3,563,787 | 2/1971 | Schneggenburger et al. . |
| 3,787,225 | 1/1974 | Roberts et al. . |
| 3,979,273 | 9/1976 | Panzera et al. . |
| 4,353,938 | 10/1982 | Sterling et al. . |
| 4,474,743 | 10/1984 | Marlett . |
| 4,855,120 | 8/1989 | Marlett . |
| 4,923,717 | 5/1990 | Gladfelter et al. . |
| 4,925,963 | 5/1990 | Marlett . |
| 4,957,726 | 9/1990 | Marlett et al. . |

OTHER PUBLICATIONS

E. Abernathy et al., *Appl. Phys. Lett.*, 56, 2654 (1990).
T. Baum et al. in *Abstracts of Papers*, Fall Meeting, Boston, Mass.; Material Research Society, Abstract No. B4.12, at p. 51 (Nov. 28–Dec. 3, 1988).
L. Dubois et al., *Surf. Sci.*, 244, 89 (1991).
W. Gladfelter et al., *Chem. Mater.*, 1, 339 (1989).
M. Green et al., *J. of Metals*, at p. 63 (Jun. 1985).
C. Heitsch, *Nature*, 195, 995 (1962).
T. Kobayashi et al., in Materials Research Society Fall Meeting, Boston, *Abstract*, at p. 136 (Nov. 28–Dec. 3, 1988).
T. Kobayshi et al., *Japan J. of App. Phys.*, 27, 1775 (1988).
R. Kovar et al., *Inorgan. Synth.*, 17, 36 (1977).
R. Levy et al., *J. Electrochem. Soc.*, 134, 37C (1987).
E. Marlett et al., *J. Org. Chem.*, 55, 2968 (1990).
G. Nechiporenko et al., in Inorganic Chemistry, Plenum Publishing Corporation, New York, at p. 1584 (1976).
J. Roberts et al., *J. Crystal Growth*, 104, 857 (1990).
J. Ruff et al., *J. Amer. Chem. Soc.*, 82, 2141 (1960).
A. Sekiguchi et al., *Japan J. App. Phys.*, 27, 364 (1988).
E. Wibert et al., *Hydrides of the Elements Main Groups I–IV*, Elsevier, publishers, Amsterdam, chapter 5, at p. 381 (1971).

*Primary Examiner*—José G. Dees
*Assistant Examiner*—Porfirio Nazario
*Attorney, Agent, or Firm*—Merchant, Gould, Smith, Edell, Welter & Schmidt

[57] ABSTRACT

This invention provides essentially pure dimethylethylamine alane, which is useful for the chemical vapor deposition of thin films of aluminum.

1 Claim, 2 Drawing Sheets

CHEMICAL VAPOR DEPOSITION OF ALUMINUM FILMS USING DIMETHYLETHYLAMINE ALANE

This invention was made with the support of the United States Government under National Science Foundation Grant No. CDR 872 1551. The Government has certain rights in the invention.

BACKGROUND OF THE INVENTION

A variety of physical and chemical deposition procedures have been used to prepare aluminum (Al) films. These methods are of interest, in part, because thin films of aluminum have many uses due to their high electrical conductivity, high reflectivity, mechanical strength, and their resistance to chemical attack. There is much current interest in generating thin films of aluminum using chemical vapor deposition (CVD), particularly resulting from applications in the microelectronics industry. In a typical CVD process, organoaluminum precursors are volatilized and then decomposed to yield aluminum, which is deposited as a film on the target substrate.

A series of stable, volatile donor-acceptor complexes of alane ($AlH_3$) have been known for many years. They can be generally represented by $D.AlH_3$, and can be readily synthesized in one step from $LiAlH_4$. These donor-acceptor complexes of alane are air sensitive, but they are not pyrophoric, as are the trialkylaluminums. Among the known donors (D) are $Me_3N$, $Et_3N$, $Me_3P$, $Me_2S$, and tetrahydrofuran (THF). See, for example, E. Wiberg et al., *Hydrides of the Elements of Main Groups I-IV*, Elsevier: Amsterdam, Ch. 5 (1971); and R. A. Kovar et al., *Inorg. Synth.*, 17, 36 (1977). Trimethylamine is unique among these donors in its ability to form a bis complex with alane, i.e., $(Me_3N)_2AlH_3$.

The use of amine-alane complexes for the vapor phase deposition of aluminum have been disclosed by T. P. Whaley et al., U.S. Pat. No. 3,206,326 (1965), and in D. R. Carley et al. U.S. Pat. No. 3,375,124 (1968). These methods, however, do not produce mirror-like coatings. Rather, less reflective "shiny" and "metallic" surfaces result. Laser-induced deposition of aluminum using aminealane complexes has been disclosed in T. H. Baum et al., *Abstracts of Papers*, Fall Meeting, Boston, Mass.; Materials Research Society: Pittsburgh, Pa., B4.12 (1988).

Trimethylamine alane (TMAA) has emerged as a promising source for aluminum in the growth of metallic aluminum films and thin films of aluminum gallium arsenide. For example, see W. L. Gladfelter et al. (U.S. Pat. No. 4,923,717); W. L. Gladfelter et al., *Chem. Mater.*, 1, 339 (1989); and E. R. Abernathy et al., *Appl. Phys. Lett.*, 56, 2654 (1990). For the growth of aluminum thin films, its advantage over triisobutylaluminum includes higher growth rates and lower required growth temperatures. In addition, it is not pyrophoric. Aluminum gallium arsenide films grown with TMAA have exhibited appreciably lower carbon and oxygen contents when compared to films grown from aluminum precursors that have direct Al-C bonds, such as triethylaluminum. (J. S. Roberts et al., *J. Crystal Growth*, 104, 857 (1990)). Despite its relatively high volatility (vapor pressure at room temperature=1.8 torr), a technological disadvantage of TMAA is that it is a solid. Thus, it is difficult to deliver it at a uniform flow rate to the substrate.

Alternative tertiaryamine complexes of alane are known, and several of these, such as triethylamine alane, tri-n-propylamine alane, and tri-n-butylamine alane, are liquids. See, J. K. Ruff et al., *J. Amer. Chem. Soc.*, 82, 2141 (1960). Unfortunately, the thermal stability of the donor-acceptor complex decreases as the stearic bulk of the donor increases. Thus, TMAA is the most stable and tri-n-butylamine is the least stable at room temperature. Triethylamine alane has been reported to give high quality aluminum films, but it is substantially less stable than TMAA See, L. H. Dubois et al., *Surf. Sci.*, 244, 89 (1991).

Therefore, a need exists for amine alane precursors for aluminum films which are both sufficiently stable and volatile, so that they can be used to provide high quality aluminum films on a variety of substrates.

SUMMARY OF THE INVENTION

The present invention provides a novel trialkylamine alane, essentially pure dimethylethylamine alane ($[(CH_3)_2(CH_3CH_2)N]AlH_3$ or DMEAA) which is useful for the deposition of aluminum films by chemical vapor deposition (CVD). While solutions of DMEAA have been prepared and used for the in situ reduction of organic carbonyls, the isolation of pure DMEAA has not previously been accomplished. See, E. M. Marlett et al., *J. Org. Chem.*, 55, 2968 (1990). The synthetic procedure followed is outlined in Scheme (1) below, and leads to distilled liquid DMEAA in good yields.

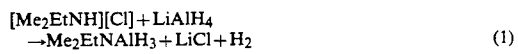

$$[Me_2EtNH][Cl] + LiAlH_4 \rightarrow Me_2EtNAlH_3 + LiCl + H_2 \quad (1)$$

No evidence was found for the existence of $(Me_2EtN)_2AlH_3$. As used herein, the term "essentially pure DMEAA" means a purity of $\geq 90\%$, preferably $\geq 95\%$, most preferably $\geq 99\%$ pure.

The results described below demonstrate that DMEAA has a blend of physical and chemical properties that render it highly useful as a liquid precursor for aluminum in chemical vapor deposition processes. In conducting the chemical vapor deposition of aluminum (Al) films, the growth of Al films was found to be unexpectedly selective for metallic surfaces. For example, using DMEAA, two strips of naked silicon on a Si<100> wafer coated with gold remained unchanged, while a 0.2 μm film of aluminum was deposited on the gold. Similar selectivity is observed with other metals such as copper, silver, zinc, nickel, tungsten, palladium, platinum and the like, i.e., with group VB, VIB, VIII, IB and IIB metals. Aluminum can also be deposited on $SiO_2$ and TiN (titanium nitride). In contrast, trimethylamine alane will deposit aluminum films on heated Si<100>surfaces, although a $TiCl_4$ pretreatment is required to yield mirror films.

Thus, the present invention also provides a method for applying an aluminum film selectively on the surface of a metallic substrate in the presence of a silicon substrate, comprising employing the techniques of chemical vapor deposition to expose a heated metallic surface and a heated silicon surface to a vapor comprising [(dimethyl)-ethyl]amine alane, so as to deposit an aluminum film on the metallic surface, while not depositing an aluminum film on the silicon (Si) surface. Pretreatment of the substrate with a Group IVB or VB metal complex, such as those disclosed in U.S. Pat. No. 4,923,717, is not employed.

Preferably, the substrate is heated to about 50°–250° C., most preferably to about 75°–225° C. Preferably the metal surface is a film of a Group IB or IIB metal which is present on the surface of the silicon substrate, wherein the silicon surface is also partly exposed. The total pressure at the substrate is maintained at about 1–5 torr during the deposition; however, this pressure does not appear to be highly critical to the deposition of the Al films, and very low pressures ($10^{-5}$ torr) have been used successfully. Films of about 0.05 μm (500 Å) to 5 μm can be readily formed under these reaction conditions, but the thickness can be varied considerably, and is dependent upon the deposition time and rate.

DETAILED DESCRIPTION OF THE INVENTION

Figure 1:
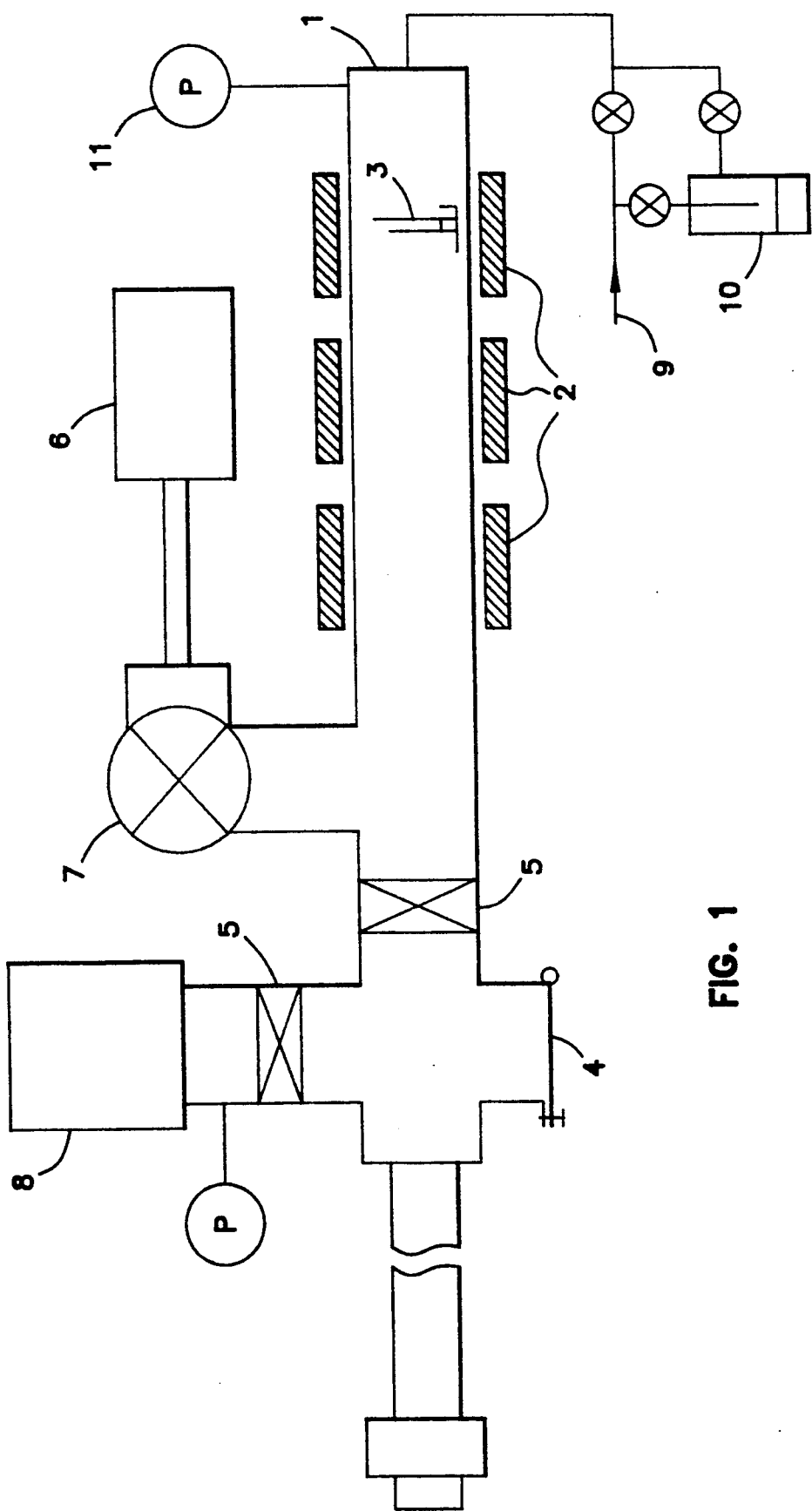
FIG. 1 is a schematic representation of the low pressure chemical vapor deposition reactor used in accordance with the present method.

The present invention will be further described by reference to the following detailed examples, wherein all reactions and subsequent manipulations involving organo-metallic reagents were performed under nitrogen using conventional Schlenk-line and glove box techniques. All solvents and reagents were purchased from Aldrich Chem. Co. (Milwaukee, Wis). The diethyl ether ($Et_2O$) was freshly distilled from Na/benzophenone ketyl under nitrogen. The dimethylethylammonium chloride was prepared by mixing the free amine, $Me_2EtN$, with a 1 M solution of HCl in $Et_2O$. Solid [$Me_2EtNH$]Cl was isolated by filtration and dried at 373K in vacuum (0.05 torr) for 3–6 hours before use.

Gas phase infrared spectra were recorded on a Mattson Cygnus 25 FTIR spectrometer. The $^1H$ NMR spectra were obtained on an IBM 200 MHz spectrometer with reference to the residual proton signal of $d_6$-benzene. The chemical shifts are reported in parts per million downfield from $Me_4Si$. Low resolution mass spectra were recorded between 30 and 70 eV on a FINNIGAN 4000 spectrometer using the direct insertion method.

Film thicknesses were measured by stylus profilimetry (Tencor Alphastep). Scanning electron micrographs were obtained on a JEOL 840 II, and Auger electron spectra were measured on a Perkin-Elmer Corp./Physical Electronics Division Model 555 spectrometer. X-ray diffraction studies were conducted using a Siemens D500 diffractometer with monochromatic (graphite) Cu Kα radiation.

EXAMPLE 1

Synthesis of $Me_2EtNAlH_3$

In a glove box, a 500 ml three neck round bottom flask was charged with $LiAlH_4$ (8.9 g, 235 mmol) and a magnetic stirring bar. Attached to the reaction flask via an appropriate glass side arm, was a Schlenk tube containing [$Me_2EtNH$]Cl (21.35 g, 195 mmol). $Et_2O$ (250 ml) was added and the resulting mixture was cooled to approximately 238 K using a saturated $CaCl_2$/Dry-ice bath. With constant stirring, the [$Me_2EtNH$]Cl was added to the reaction mixture over 1.5 hr. The reaction mixture was slowly warmed to 273 K over 1 hr and then stirred for 2 hr. Then the resulting reaction mixture was filtered through a medium-porosity glass frit to remove the solids. The reaction flask was washed with $Et_2O$ (2×15 ml) and the filtrates were collected. The $Et_2O$ solvent was removed slowly in vacuo at 273 K until approximately 30 ml of liquid remained. Gas phase infrared spectra were obtained of the volatiles from the reaction mixture to monitor the removal of the $Et_2O$ solvent. At the point where no $Et_2O$ remained, 16.8 g of $Me_2EtNAlH_2$ (84% yield), was collected by vacuum distillation at 303 K. Anal Calc. for $C_4H_{14}NAl$: C, 46.58; H, 13.68; N, 13.58; Al, 26.16. Found: C, 46.45; H, 13.51; N, 13.68; Al, 25.90. IR (Gas phase): υAl—H $=1790$ cm$^{-1}$. $^1H$ NMR (δ, $d_6$—benzene); 4.0 (br, 3H, $AlH_3$), 2.21 (q, 2H, $CH_2$), 1.84 (S, 6H, $N(CH_3)$), 0.69 (t, 3H, $CH_2CH_3$). Mass spectrum m/z: 102 ($M^+$—H). Melting point: 278 K. Vapor pressure: 1.5 torr at 297 K (24° C.).

EXAMPLE 2

Chemical Vapor Deposition of Aluminum Films

A. Reactor Description and Deposition Procedure

The aluminum depositions were carried out using the apparatus shown in FIG. 1, which was constructed of stainless steel components compatible with ultra-high vacuum (UHV) operation. The reactor consisted of a Pyrex tube (1) (6.6 cm ID) which was heated over 61 cm of its length by a 3-zone furnace (2). A profile of the substrate temperature in the reactor was made by attaching a thermocouple between two substrates (3), i.e., silicon wafers, and allowing the system to equilibrate under the same flow and total pressure conditions experienced during a deposition. Both substrate positioning and process control combined to give a temperature reproducibility of ±2 K even near the reactor entrance where the temperature rise was steep. A temperature profile across the silicon substrate revealed a uniform temperature at 443 K (170° C).

A load-lock system comprising a wafer loading door (4), and gate valves (5) was used to introduce the substrates Si<100>) into the heated zone. The entire system was then evacuated by mechanical vacuum pump (6), linked to the tube by a right-angle throttle valve (7), and then by a turbomolecular pump (8) to a background pressure of $2\times10^{-7}$ torr. The Si wafers were precleaned successively in trichloroethylene, acetone, methanol, dilute HF and deionized water. Following drying in an $N_2$ stream, they were introduced into the load-lock system. Copper substrates were cleaned with methanol. The gold films (600 Å) were prepared by evaporation onto precleaned silicon wafers and used without any further cleaning. Following substrate introduction and evacuation, the system was purged with Pd-purified hydrogen (100 sccm) and equilibrated to the desired deposition temperature. The pumping speed was adjusted using the right angle valve (7) to give a constant total pressure of 3.0 torr as measured by a capacitance manometer. Deposition was initiated by diverting the $H_2$ flow (9) through the precursor vessel (10). The total pressure in the system increased to 3.3 to 3.4 torr and remained constant throughout the deposition as measured by pressure gauge (11). The temperature of the precursor vessel was maintained at room temperature using a water bath (not shown).

B. Results

Using the conditions outlined in part A, above, depositions were conducted in the temperature range from 373 to 623 K (100°–350° C.). At 443K (170° C.) the substrate position was 2.5 cm from the beginning of the heated portion of the furnace. Below 473 K (200° C.), selectivity was observed.

The growth of aluminum was found to be unexpectedly selective for metallic surfaces. The best demonstration of the selectivity of the film growth was observed with the gold-coated silicon wafers. Two strips of silicon, formed by masking during the evaporation of the initial gold film, remained unchanged while a 0.2 μm film of aluminum was deposited on the gold. Scanning electron microscopy (SEM) of the boundary region between the silicon and gold surface showed a line with a roughness similar to the size of the aluminum grains. There were also a substantial number of isolated aluminum grains in the silicon region bordering the gold film. It is believed that this region contained isolated gold nuclei that formed as a result of imperfect shadowing during the evaporation. SEM of the edge of a similar gold film prior to growth of an aluminum coating established that islands of gold were present in this border region. The growth rate of aluminum films on copper at 443 K was 0.15 μm/min.

Figure 2:
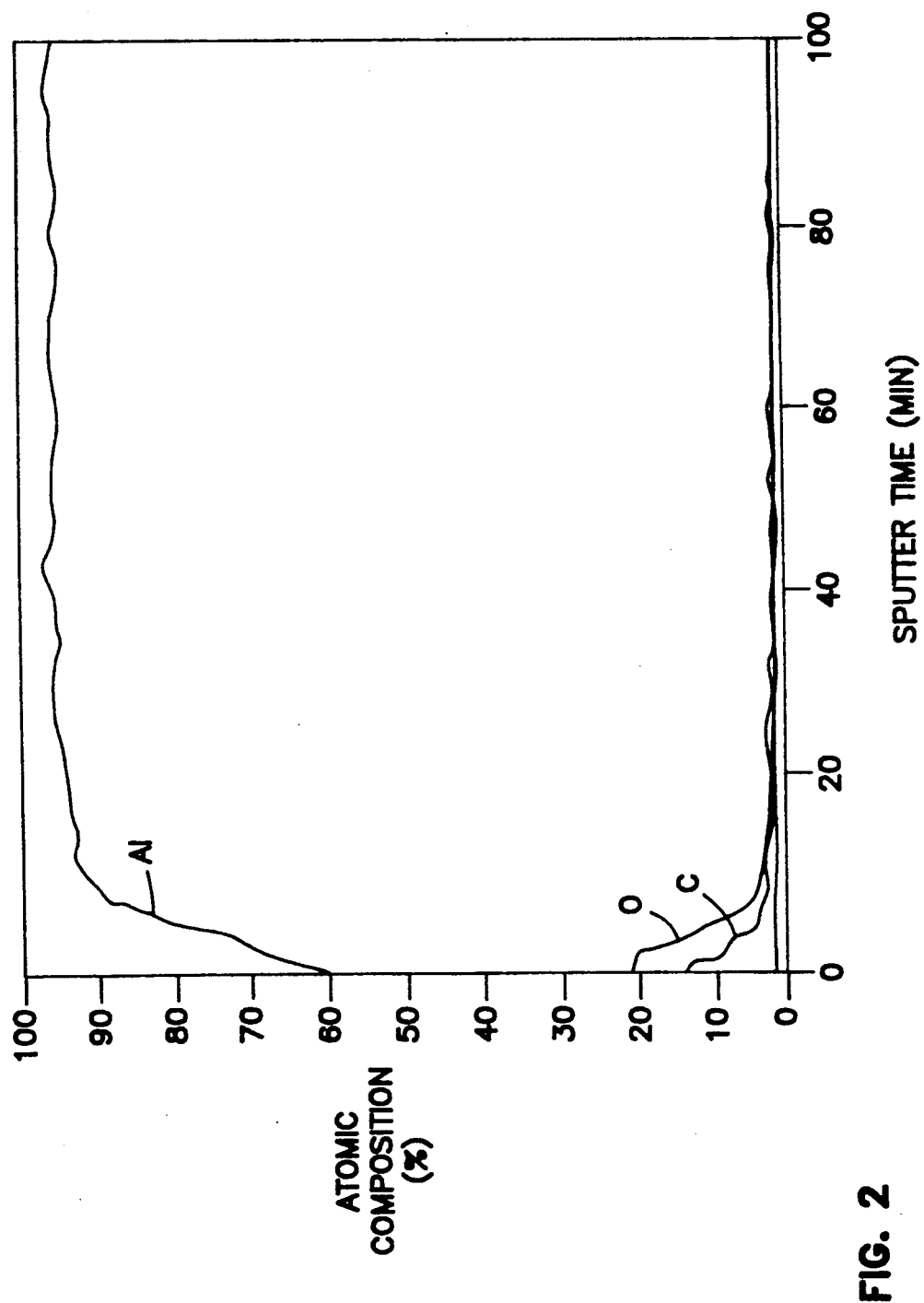
FIG. 2 depicts the depth profile of the auger electron spectrum of a typical Al film deposited on a gold film using DMEAA.

FIG. 2 shows the Auger electron spectral data of an Al film on gold as a function of argon ion sputtering time. As soon as the top layers of material were removed all impurity levels dropped below the limits of detection. X-ray diffraction patterns established the films were polycrystalline aluminum with no preferred orientation.

EXAMPLE 3

Using deposition procedures similar to those of Example 2, (10 sccm DMEAA, 100 mT reactor pressure), Al films were deposited on the substrates listed on Table 1, below.

TABLE 1

| Substrate Temp. (°C.) | Max. Deposition Rate Å/min, on: | | | |
|---|---|---|---|---|
| | Si | SiO$_2$ | TiN | W |
| 115 | 73 | 0 | <1 | 0 |
| 140 | 54 | 83 | 132 | 18 |
| 162 | 28 | 74 | 56 | 23 |

All patents, patent documents and other publications cited herein are disclosed by reference herein. The invention has been described with reference to various specific and preferred embodiments and techniques. However, it should be understood that many variations and modifications may be made while remaining within the spirit and scope of the invention.

What is claimed is:

1. Essentially pure [(CH$_3$)$_2$(CH$_3$CH$_2$)N]AlH$_3$.

* * * * *

UNITED STATES PATENT AND TRADEMARK OFFICE
CERTIFICATE OF CORRECTION

PATENT NO. : 5,191,099
DATED : March 2, 1993
INVENTOR(S) : Gladfelter et al.

It is certified that error appears in the above-identified patent and that said Letters Patent is hereby corrected as shown below:

Column 1, lines 7-9, "United States Government under national Science Foundation Grant No. CDR 872,1551. The Government has certain rights in the invention" should read --National Science Foundation under grant number CDR 8721551. The U.S. Government has rights in the invention.--

Column 4, line 9, "$Me_2EtNAlH_2$," should read --$Me_2EtNAlH_3$,--.

Column 4, line 44, after the word "substrates" insert --(Si<100>, and Cu and Au films evaporated on--.

Signed and Sealed this

Twenty-fifth Day of January, 1994

Attest:

BRUCE LEHMAN

Attesting Officer

Commissioner of Patents and Trademarks